(12) United States Patent
Rawat et al.

(10) Patent No.: US 10,143,602 B2
(45) Date of Patent: *Dec. 4, 2018

(54) BONDING PATTERN FOR DISPOSABLE ABSORBENT ARTICLES

(71) Applicant: The Procter & Gamble Company, Cincinnati, OH (US)

(72) Inventors: Digvijay Rawat, Cincinnati, OH (US); Ronda Lynn Glassmeyer, Cincinnati, OH (US); Keith Joseph Stone, Fairfield, OH (US); Pietro Cecchetto, Fairfield, OH (US); Lennie Cruz Murphy, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,585

(22) Filed: Apr. 21, 2017

(65) Prior Publication Data

US 2017/0216107 A1    Aug. 3, 2017

Related U.S. Application Data

(63) Continuation of application No. 13/952,335, filed on Jul. 26, 2013, now Pat. No. 9,655,791, which is a
(Continued)

(51) Int. Cl.
*B32B 3/24*     (2006.01)
*A61F 13/515*   (2006.01)
(Continued)

(52) U.S. Cl.
CPC .......... *A61F 13/515* (2013.01); *A61F 13/472* (2013.01); *A61F 13/5116* (2013.01); *A61F 13/5121* (2013.01); *A61F 13/51104* (2013.01); *Y10T 428/24331* (2015.01); *Y10T 428/24826* (2015.01); *Y10T 428/24851* (2015.01)

(58) Field of Classification Search
CPC ....................... Y10T 428/24826; A61F 13/515
See application file for complete search history.

(56) References Cited

U.S. PATENT DOCUMENTS

| 4,854,984 A | 8/1989 | Ball et al. |
| 7,056,404 B2 | 6/2006 | McFall et al. |

(Continued)

FOREIGN PATENT DOCUMENTS

| JP | 2004-298454 | 10/2004 |
| KR | 2001-0108479 | 12/2001 |

(Continued)

OTHER PUBLICATIONS

International Search Report, dated Feb. 13, 2012, 13 pages.

*Primary Examiner* — William P Watkins, III
(74) *Attorney, Agent, or Firm* — Andres Ernesto Velarde

(57) ABSTRACT

In accordance with an embodiment of the disclosure, an article includes a first web and second web underlying the first web. The article further includes a bonding pattern. The bonding pattern includes a plurality of discrete bonding points and a sized spacing between each adjacent bonding point sufficient to have inscribed therein a circle having a diameter of about 1 mm to about 12 mm. The bonding pattern is located solely in one of the front end region or the back end region.

20 Claims, 6 Drawing Sheets

Related U.S. Application Data continuation-in-part of application No. 13/426,049, filed on Mar. 21, 2012, now Pat. No. 9,675,500, which is a continuation of application No. PCT/US2011/053609, filed on Sep. 28, 2011.

(60) Provisional application No. 61/388,733, filed on Oct. 1, 2010.

(51) Int. Cl.
*A61F 13/511* (2006.01)
*A61F 13/472* (2006.01)
*A61F 13/512* (2006.01)

(56) References Cited

U.S. PATENT DOCUMENTS

| | | |
|---|---|---|
| 7,521,588 B2 | 4/2009 | Stone et al. |
| 7,655,176 B2 | 2/2010 | Stone et al. |
| 2004/0121120 A1 | 6/2004 | Gray et al. |
| 2004/0122395 A1 | 6/2004 | Stone et al. |
| 2005/0087292 A1 | 4/2005 | McFall et al. |
| 2005/0170729 A1 | 8/2005 | Stadelman et al. |
| 2010/0230857 A1 | 3/2010 | Muhs et al. |
| 2010/0230858 A1 | 3/2010 | Stone et al. |
| 2010/0230866 A1 | 3/2010 | Gray et al. |
| 2010/0230867 A1 | 3/2010 | Gray et al. |

FOREIGN PATENT DOCUMENTS

| | | |
|---|---|---|
| WO | WO 00/59438 | 10/2000 |
| WO | WO 2004/108037 | 12/2004 |
| WO | WO 2010/104996 | 9/2010 |
| WO | WO 2011/118473 | 9/2011 |

BONDING PATTERN FOR DISPOSABLE ABSORBENT ARTICLES

FIELD OF THE INVENTION

The invention relates to an article having a bonding pattern for bonding together at least two webs of material. More particularly, this invention relates to an article having a bonding pattern for bonding together two webs of material such that tearing of the webs during normal use of the article can be prevented.

BACKGROUND OF THE INVENTION

Absorbent articles such as sanitary napkins, pantiliners, tampons, absorbent interlabial devices, disposable diapers, incontinence products, and bandages are designed to absorb and retain liquid and other discharges from the human body and to prevent body and clothing soiling. In the manufacture of absorbent articles, it is generally necessary to bond the components that will form the absorbent article together in order to form the finished product. For example, topsheet materials can be bonded to a secondary layer, for example, a secondary topsheet material, to provide added strength and reinforcement to the topsheet material.

Some web materials, such as low cost soft and silky tactile web materials (for example, for use as topsheet materials), have weak material strength in the cross direction. It has been observed that when typical bonding patterns are used to bond together such web materials, tearing occurs during use between bonding points. While, increasing the number of bonding points bonding the web materials together would decrease the amount of unbounded material that is susceptible to the tearing problem, such an increase would undesirably increase the stiffness of the material, making it less comfortable and less desirable to a consumer using a product having the bonded webs. Thus, there remains a desire and need in the art to develop an article having sufficient bonding between the web materials, particularly when using a low cost web material with weak material strength in the cross direction, so as to prevent tearing of the web material during use, without undesirably increasing the stiffness of the web material.

SUMMARY OF THE INVENTION

A sanitary napkin is disclosed. The sanitary napkin includes a first end region and a second end region comprising a bonding pattern. The first end region and the second end region are between 10% and 30% of the total area of the sanitary napkin. The sanitary napkin further includes a central region that is between 40% to about 80% of the total surface area of the sanitary napkin. The bonding pattern adhering together a first web and a second web includes a plurality of discrete bonding points and a sized spacing between each adjacent bonding point sufficient to have inscribed therein a circle having a diameter of about 3 mm to about 12 mm. The bonding pattern is located solely in one of the front end region or the back end region.

An article is further disclosed. The article includes a first end region and a second end region comprising a bonding pattern. The first end region and the second end region are between 10% and 30% of the total area of the article. The bonding pattern adhering together a first web and a second web includes a plurality of discrete bonding points and a sized spacing between each adjacent bonding point sufficient to have inscribed therein a circle having a diameter of about 3 mm to about 12 mm. The bonding pattern is located solely in one of the front end region or the back end region. The article is a sanitary napkin.

Figure 1:
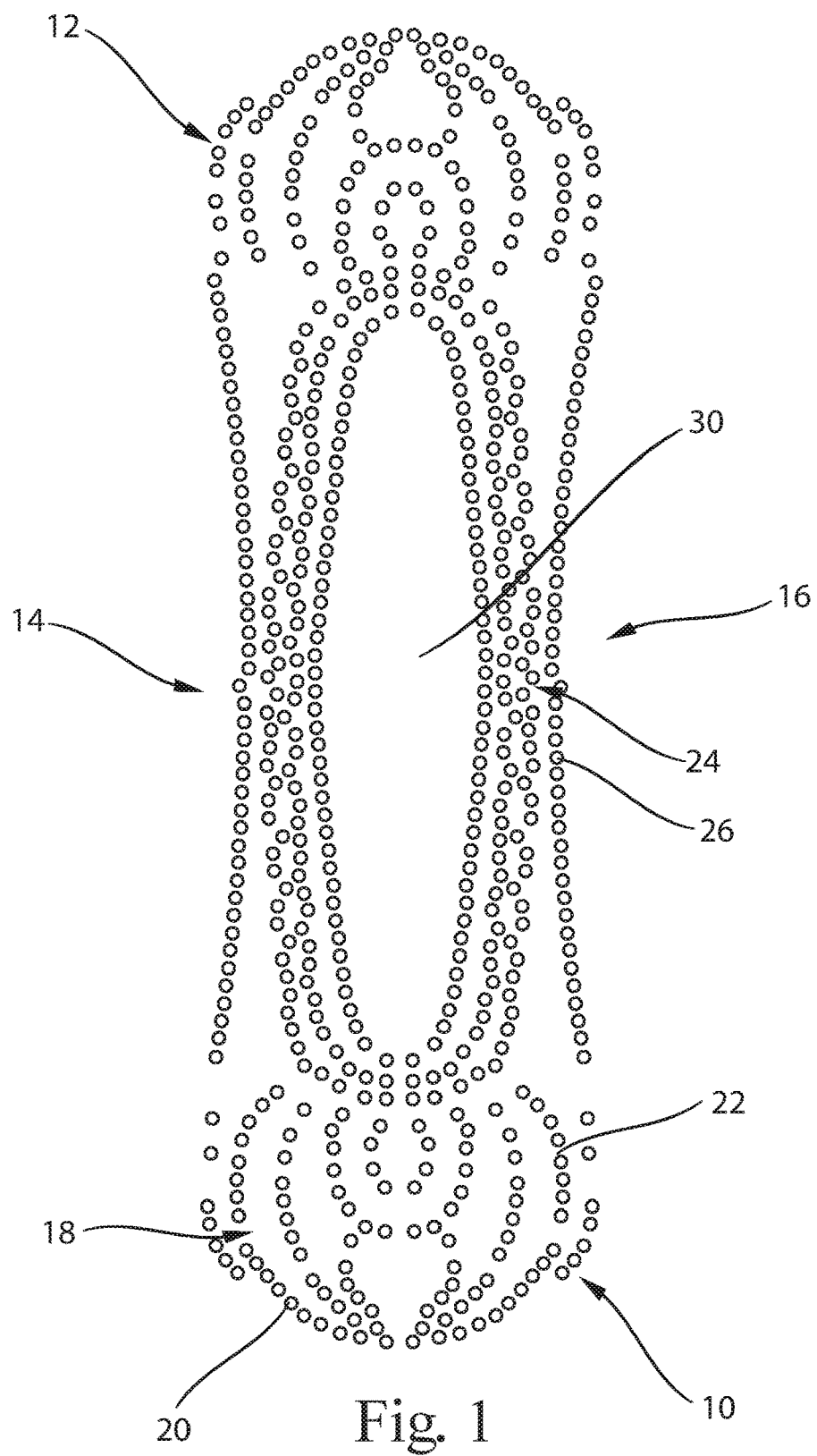
FIG. 1 is a schematic illustration of a bonding pattern in accordance with an embodiment of the disclosure.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Disclosed herein is an article having first and second web materials, portions of which are bonded together using a bonding pattern that overcomes one or more of the aforementioned shortcomings of the prior art. For example, the article in accordance with embodiments of the disclosure advantageously includes a bonding pattern which can prevent tearing of the first web material during use of the article without undesirably affecting the tactile feel of the webs.

An article in accordance with an embodiment of the disclosure includes a first web and a second web underlying the first web. The first web includes a precursor web having a pattern of discrete substantially columnar protruded extensions. The protruded extension can extend, for example, from a first surface of the first web, which is disposed opposite the surface of the first web which contacts the second web. The protruded extensions each have a sidewall defining an open proximal portion and a closed distal portion. In various embodiments, first web can include macroapetures to render the first web fluid permeable. The first and second webs each include first and second end regions, a central region, and first and second side regions disposed between the first and second end regions which may be part of the central region. The article includes a bonding pattern, which adheres together at least one of the first end regions of the first and second webs and the second end regions of the first and second webs. The bonding pattern includes a plurality of discrete bonding points and a sized spacing between each adjacent bonding point, which is sufficient to have inscribed therein a circle having a diameter of about 1 mm to about 12 mm.

The first end regions of the first and second webs can be about 10% to about 30% of the total area of the article. For example, the first end regions of the first and second webs can be about 25% of the total surface area of the article. The second end regions of the first and second web can be about 10% to about 30% of the total area of the article. For example, the second end regions of the first and second webs can be about 25% of the total surface area of the article. The first and second webs further include first and second side regions. The first side regions can be about 10% to about 30% of the total area of the article, and the second side regions can be about 10% to about 30% of the total area of the article. For example, the first and second side regions can each be about 25% of the total area of the article.

The central region can be about 80% to about 40% of the total area of the article. For example, the first end region can be about 25% and the second end region can be about 10% with a central region that is about 65% of the total area of the article. The central region may be broken up into bisecting sections along a longitudinal axis of the article.

The article can be divided into portions along the longitudinal axis. The portions may or may not be equal in area. The portions can be equal in length along the longitudinal axis. In a non-limiting embodiment, an article may be broken up into, for example, 15, 14, 13, 12, 11, 10, 9, 8, 7, 6, 5, 4, 3, or 2 portions that are equal in length along the longitudinal axis.

First Web

The first web materials suitable for use in the article in accordance with an embodiment of the disclosure are advantageously lower cost materials than typical topsheet materials, such as for example, the topsheet material commercially available as the soft dry weave cover used in the ALWAYS ULTRATHIN pads (Procter & Gamble). However, such web materials tend to stick to the skin of the user during use and have low yield points, which can result in tearing of the web between bonding points when such web materials are incorporated into an absorbent article. For example, as compared to the commercially available soft dry weave cover used in the ALWAYS ULTRATHIN pads, the first web material exhibits significantly increased stick to skin and has decreased yield strength.

Suitable first web materials are described in U.S. Pat. No. 7,521,588 and U.S. Patent Publication Nos. 2010/0230857, 2010/0230858, 2010/0230866, and 2010/0230867, the disclosures of which are incorporated herein in their entireties. The first web includes a precursor web, which can include, for example, a plurality of discrete protruded extensions extending only from a first surface of the precursor web. The first web can further include macroapertures. In one embodiment, the first web includes macroapertures and does not include discrete protruded extensions.

Examples of films suitable for use as the precursor web include films of low density polyethylene (LDPE), linear low-density polyethylene (LLDPE), and blends of linear low-density polyethylene and low density polyethylene (LDPE/LLDPE). The precursor material can have a thickness of about 10 microns to about 25 microns. For example, suitable precursor web thicknesses include about 10, 11, 12, 13, 14, 15, 16, 17, 18, 19, 20, 21, 22, 23, 24, 25 microns. One material found suitable for use as the precursor web is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882).

The protruded extensions have sidewalls defining an open proximal portion and a closed distal portion. The discrete protruded elements can form hair-like fibrils that extend from a first surface of the web. The discrete protruded elements impart a soft feel to the web material, making it more desirable for use in an absorbent article, and particularly for use as a topsheet material in an absorbent article. The protruded extensions can be formed integral with the film, and can be formed by permanent local plastic deformation of film. The protruded extensions have a height measured from a minimum amplitude between adjacent protruded extensions to a maximum amplitude at the closed distal portion. The protruded extensions can have a diameter, which for a generally cylindrical structure is the outside diameter at a lateral cross-section. By "lateral" is meant generally parallel to the plane of the first surface of the web. For non-uniform lateral cross-sections, and/or non-cylindrical structures, the diameter is measured as the average lateral cross-sectional dimension at ½ the height of the protruded extension. Thus, for each protruded extensions, an aspect ratio, defined as height/diameter, can be determined. The protruded extensions can have an aspect ratio of at least 0.5. Other suitable aspect ratios include, for example, about 0.5, 1, 1.5, 2, 2.5, and 3.

The diameter of protruded extensions can remain constant or can decrease with increasing amplitude (amplitude increases to a maximum at the closed distal end). For example, the diameter, or average lateral cross-sectional dimension, of protruded extensions can be a maximum at the proximal portion and the lateral cross-sectional dimension steadily decreases to distal end. The protruded extensions can have an average cross-section diameter of about 50 microns to about 130 microns, about 60 microns to about 120 microns, about 70 microns to about 110 microns, and about 80 microns to about 100 microns. Other suitable average cross-section diameters include about 50, 60, 70, 80, 90, 100, 110, 120, and 130 microns.

The area density of the protruded extensions, which is the number of protruded extensions per unit area of the first surface of the web, can be optimized for use in absorbent articles. In general, the center-to-center spacing can be optimized for adequate tactile impression, while at the same time minimizing fiber-to-fiber entrapment of fluid. Currently, it is believed that a center-to-center spacing of about 100 microns to 250 microns is optimal for use in sanitary napkins. Minimizing entrapment of menses between fibers improves the surface cleanliness of the sanitary napkin, which, in turn improves the cleanliness and skin health of the wearer.

Figure 5:
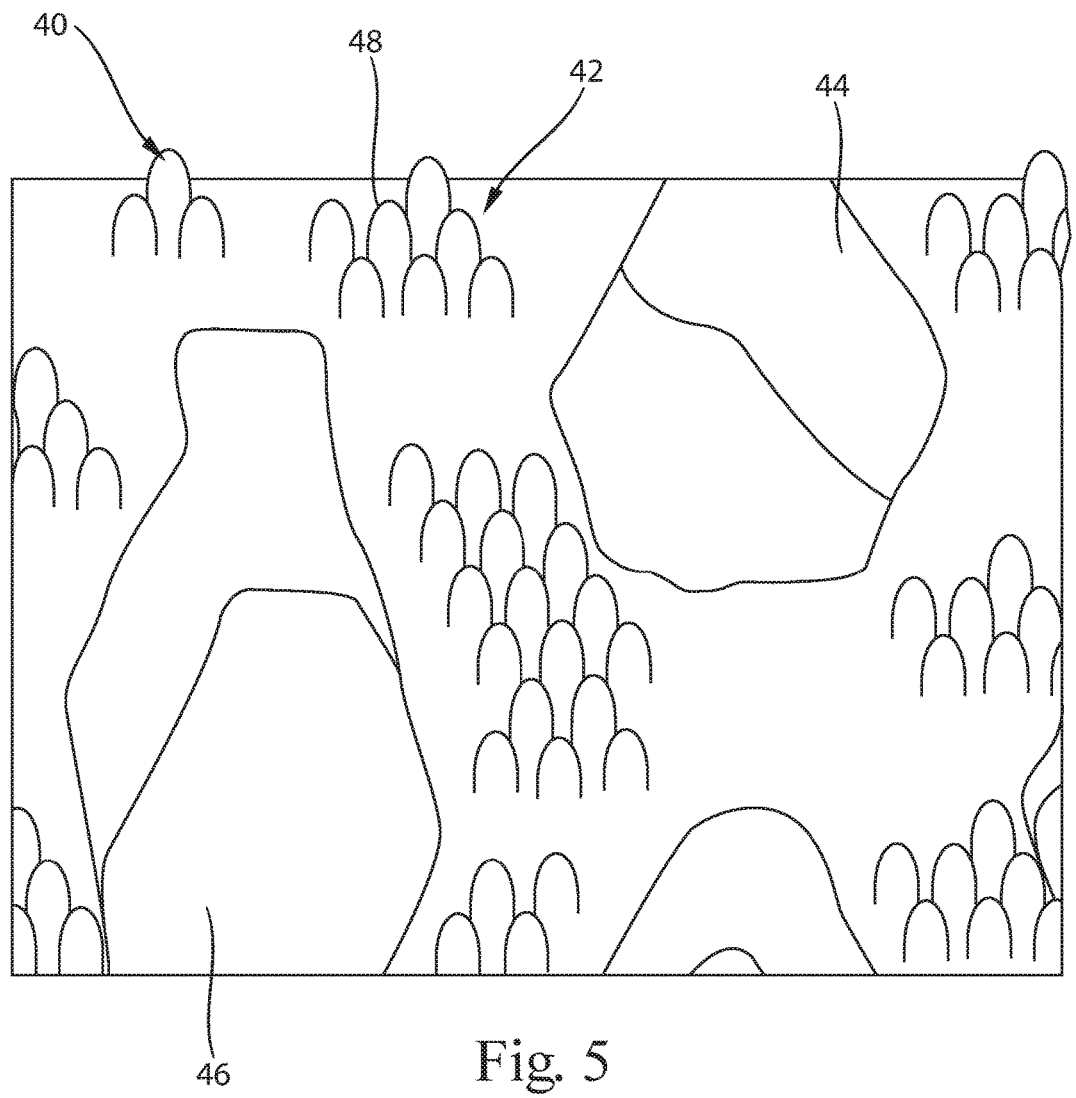
FIG. 5 is a schematic illustration of a first web material suitable for use in an embodiment of the disclosure.

The first web can further include a plurality of apertures to allow the first web to be liquid permeable. For example, the apertures can be macroapertures which are formed by a multiplicity of interconnecting members, such as fiber like elements, that are interconnected to one another to define a continuous first surface of the web. The macroapetures can have any suitable shape. For example, the macroapertures can polygon-shaped. In one embodiment, the macroapetures have a hexagon shape. The macroapertures can have a diameter in a range of about 300 microns to about 1000 microns, about 400 microns to about 900 microns, about 500 microns to about 800 microns, or about 600 microns to about 700 microns. In one embodiment, the first web includes macroapetures and discrete protruded extensions. The apertures can extend from the first surface of the web to a second surface of the web so as to extend in an opposite direction as the protruded extensions and the discrete protruded extensions can be disposed only the first surface of the web. Referring to FIG. 5, in one embodiment, the first web 40 can include macroapetures 46 with discrete protruded extensions 48 extending only from a top 42 (i.e., first) surface of the web. The sidewalls 44 of the macroapetures 46 remain free from discrete protruded extensions 48.

Second Web

The second web can be any suitable web material. For example, the second web can be a secondary topsheet material, which can impart added strength and structural reinforcement to the first web material. The second web can include, for example, absorptive materials. In one embodiment, the second web includes a nonwoven layer formed by a mix of synthetic fibers and cellulose to impart absorptive properties to the second web material. An example of a suitable secondary topsheet material for use as the second web is REXCELL PTCX 077 (Rexcell AB).

Bonding Pattern

Referring to FIG. 1, the bonding pattern 18 adheres together at least one of the first end regions 10 of the first and second webs and the second end regions 12 of the first and second webs. The bonding pattern 18 includes a plurality of discrete bonding points 20. The bonding patterning 18 further includes a sized spacing 22 between adjacent bonding points sufficient to have inscribed therein a circle having a diameter of about 1 mm to about 12 mm. The circle is inscribed so as to be tangent to the adjacent bonding points. Other suitable diameters include about 2 mm to about 10 mm, about 3 mm to about 10 mm, and about 4 mm to about 8 mm. For example, the sized spacing can be sufficient to have inscribed therein a circle having a diameter of about 1 mm, 2 mm, 3 mm, 4 mm, 5 mm, 6 mm, 7 mm, 8 mm, 9 mm, 10 mm, 11 mm, and 12 mm As used herein, "adjacent bonding points" refers to two bonding points, which can be connected by a straight line that does not intersect or otherwise touch another bonding point. Adjacent bonding points are also disposed in the same end region (the first end region 10 or the second end region 12). Such a sized spacing advantageously provides a bonding pattern 18 in which the first and second webs are sufficiently adhered together such that the first web does not exhibit tearing during use of the article, while allowing the first and second webs to remain sufficiently soft and flexible so that the article remains soft and silky to the touch.

Figure 2:
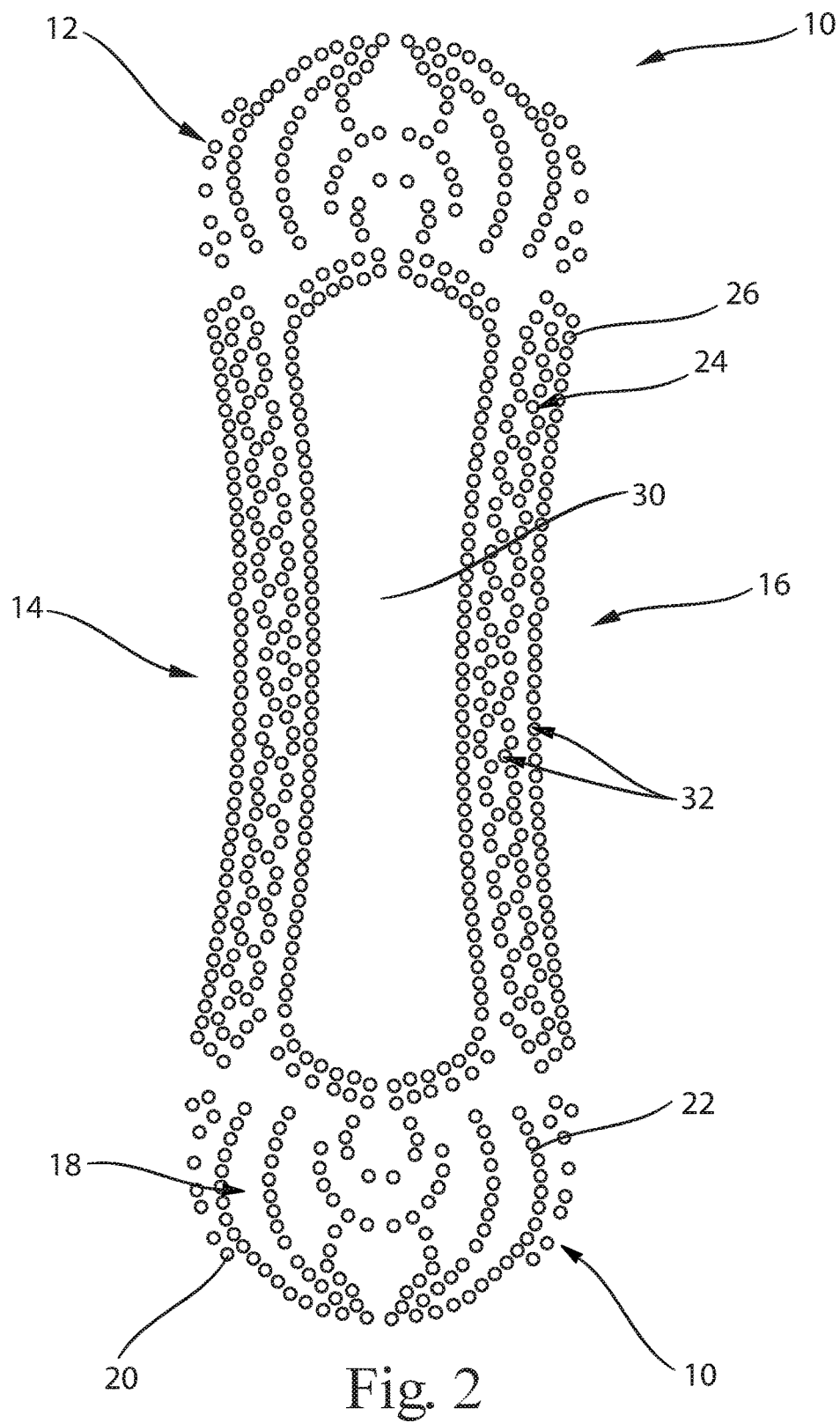
FIG. 2 is a schematic illustration of a bonding pattern in accordance with another embodiment of the disclosure.
Figure 3:
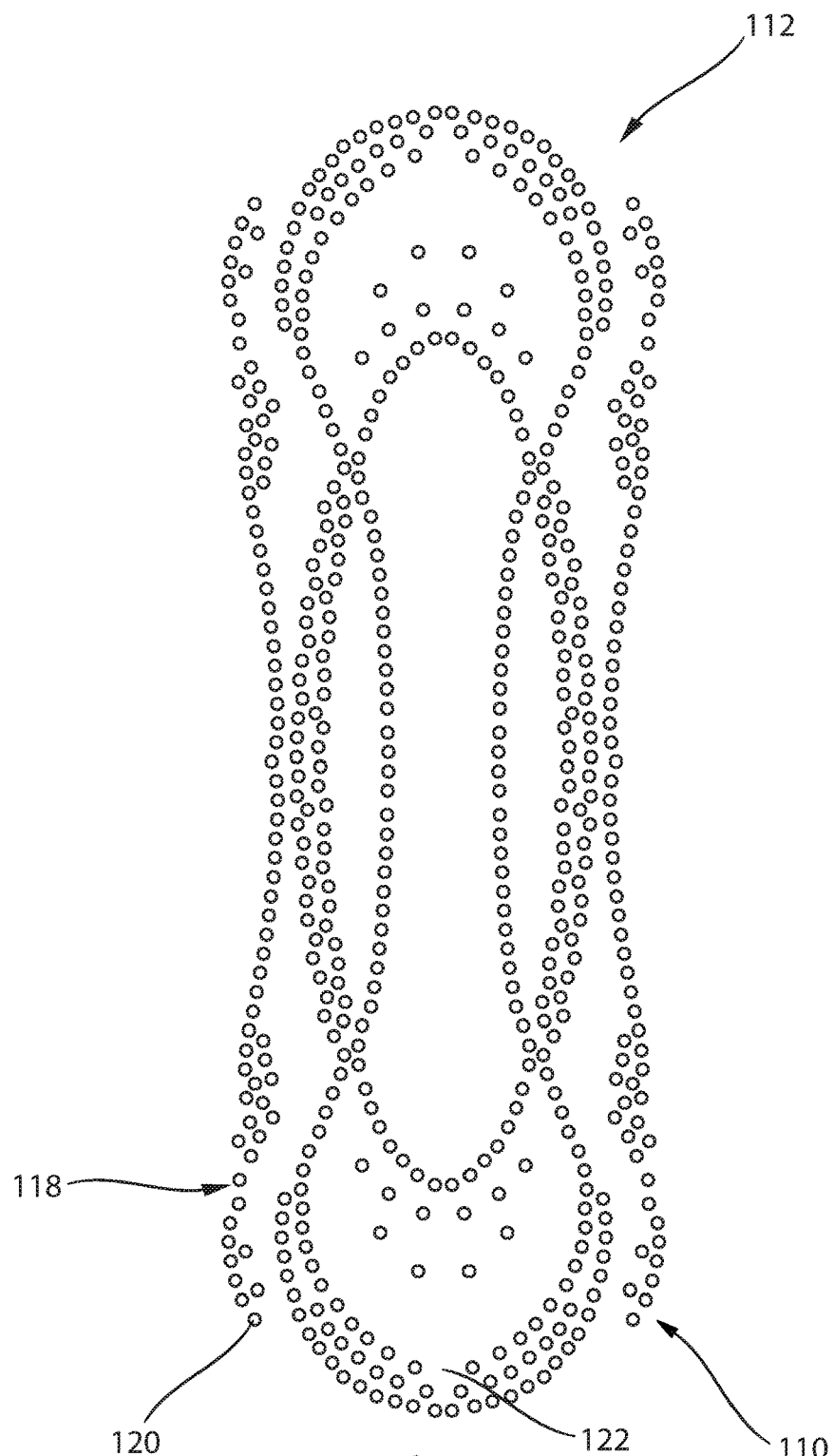
FIG. 3 is a schematic illustration of a prior art bonding pattern for which topsheet tearing is observed.
Figure 4:
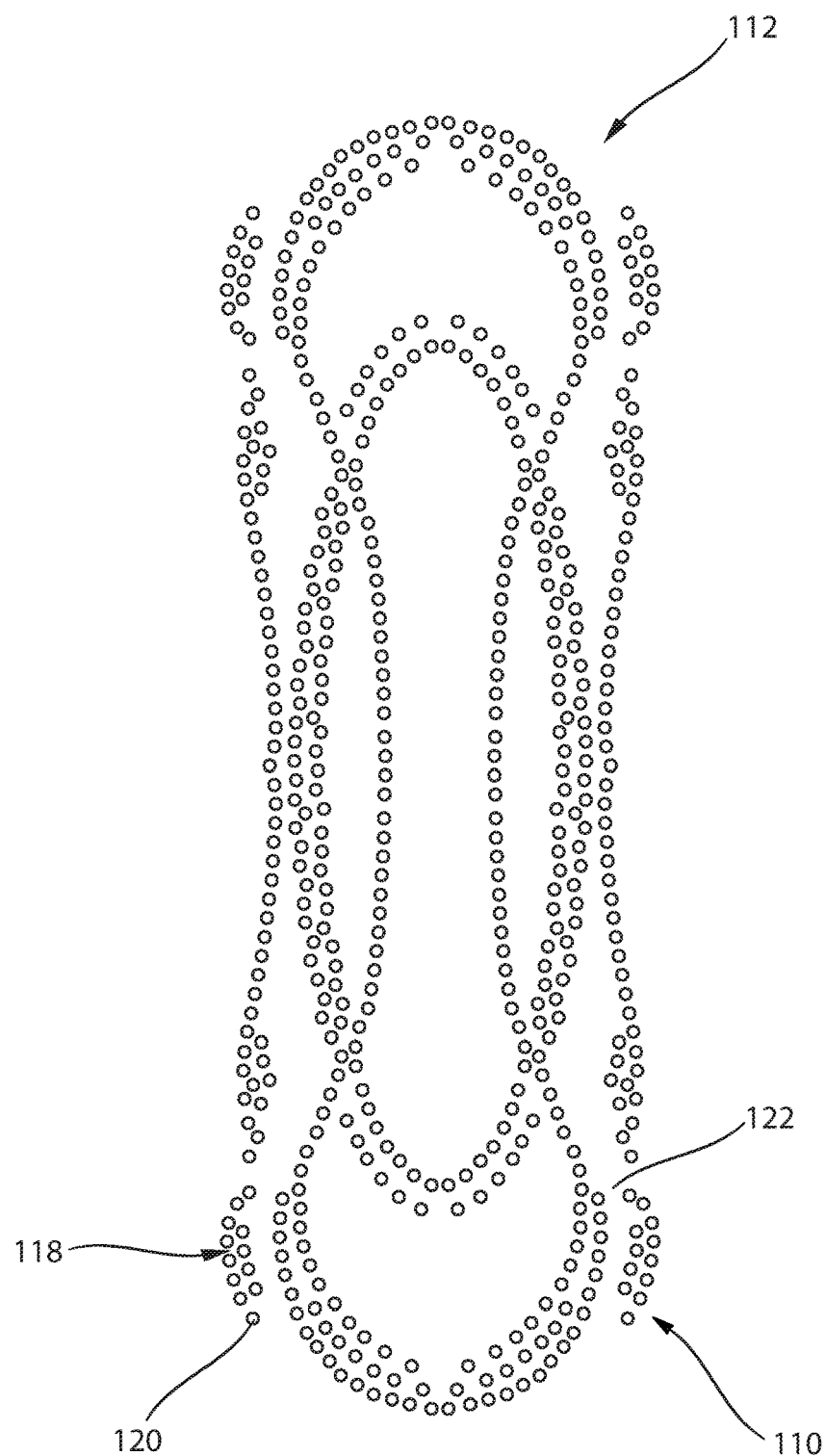
FIG. 4 is a schematic illustration of a prior art bonding pattern for which topsheet tearing is observed.

FIGS. 3 and 4 illustrate prior art bonding patterns. Common features of the bonding pattern 18 of FIGS. 3 and 4 are labeled with common reference numbers from FIGS. 1 and 2 having a leading "1." The prior art articles include first and second end regions 110 and 112, respectively, having a bonding pattern 118 adhering together the first and second webs. The bonding pattern 118 includes a plurality of bonding points 120. However, the sized spacing 122 between adjacent bonding points 120 can vary drastically between adjacent bonding points. It has been observed that when using such bonding patterns 118, absorbent articles having the first web material disclosed herein exhibit tearing during use. Such a prior art bonding pattern 118 has larger spacing 122 between some of the adjacent bonding points, which allows larger unbounded areas of the first web that are susceptible to tearing. A comparison of FIGS. 3 and 4 to FIG. 1 illustrates that the bonding pattern 18 in accordance with the embodiment of the disclosure has a sized spacing 22 designed to decrease the size of the unbounded areas of the first web, while not resulting in an increase in the number of bonding points 20 which would render the article stiff to the touch and undesirable for use.

The bonding pattern 18 can cover about 10% to about 20%, about 15% to about 20%, about 12% to about 18%, or about 14% to about 16% of the total surface area of the first or second end regions 10 and 12, respectively, of the first and second webs. For example, the bonding pattern 18 can cover about 10%, 11%, 12%, 13%, 14%, 15%, 16%, 17%, 18%, 19%, or 20% of the total surface area of the first and second end regions 10 and 12, respectively.

The bonding pattern 18 can adhere together only the first end regions 10 of the first and second webs. Alternatively, the bonding pattern 18 can adhere together only the second end regions 12 of the first and second webs. In yet another embodiment, the bonding pattern 18 can adhere together both the first and second end regions 10 and 12, respectively, of the first and second webs. It has been observed that tearing of the first web during use most often occurs in the back end of the article. Thus, for articles that do not have defined front and back ends, it can be advantageous to provide the bonding pattern 18 in both the first and second end regions 12 of the article.

The article can further include a second bonding pattern 24 that adheres together at least one of the first sides regions 14 of the first and second webs and the second side regions 16 of the first and second webs. The second bonding pattern 24 includes a plurality of discrete second bonding points 26. The center-to-center spacing between each adjacent second bonding point 26 preferably is about 1 mm to about 3 mm, about 1.5 mm to about 2 mm, about 1.2 mm to about 1.8 mm, and about 1.1 mm to about 1.5 mm. Other suitable center-to-center spacings include about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3 mm.

Referring to FIG. 2, the second bonding pattern 24 can have the plurality of second bonding points 26 arranged in a series of longitudinal lines 32. The spacing between adjacent longitudinal lines can be about 1 mm to about 5 mm, about 2 mm to about 4 mm, about 2 mm to about 3 mm, or about 3 mm to about 5 mm. Other suitable spacings between adjacent longitudinal lines can be about 1, 1.5, 2, 2.5, 3, 3.5, 4, 4.5, and 5 mm.

The second bonding pattern 24 can cover about 10% to about 20%, about 15% to about 20%, about 12% to about 18%, or about 14% to about 16% of the total surface area of the first or second side regions 14 or 16, respectively, of the first and second webs. For example, the second bonding pattern 24 can cover about 10%, 11%, 12%, 13%, 14%, 15%, 16%, 17%, 18%, 19%, or 20% of the total surface area of the first and second side regions 14 and 16, respectively. In one embodiment, the second bonding pattern 24 can be arranged on the side regions such that a center portion 30 of the article remains free of bonding points. For example, the second bonding pattern 24 can bond portions of the first and second side regions 14 and 16, respectively, of the first and second webs, leaving a center portion 30 of the article free of second bonding points 26. In yet another embodiment, the second bonding pattern 24 can bond only the first side region 14 or only the second side region 16 of the first and second webs.

The bonding points 20 in the first and second end regions 10 and 12, respectively, of the article and the second bonding points 26 can have any suitable shape including, for example, circular, elliptical, triangular, rectangular, and combinations thereof. These bonding points can have a diameter of about 1 mm to about 2 mm, about 1.1 mm to about 1.8 mm, about 1.4 mm to about 1.6 mm, and about 1.6 mm to about 2 mm. Other suitable bonding point diameters include, for example, about 1, 1.1, 1.2, 1.3, 1.4, 1.5, 1.6, 1.7, 1.8, 1.9, or 2 mm.

These bonding points can be formed by any known means. For example, these bonding points can be formed using adhesive or by melt fusing the first and second webs at discrete bonding points. Suitable examples of methods of bonding web materials can be found in U.S. Pat. Nos. 7,056,404 and 4,854,984.

The first bonding pattern 18 and second bonding pattern 24 may form a combined third bonding pattern 60.

The bonding pattern 60 can cover about 5% to about 20%, about 15% to about 20%, about 12% to about 18%, or about 14% to about 16% of the total surface area of the article 10 of the first and second webs. For example, the bonding pattern 60 can cover about 5%, 6%, 7%, 8%, 9% 10%, 11%, 12%, 13%, 14%, 15%, 16%, 17%, 18%, 19%, or 20% of the total surface area of the article 10.

Figure 6:
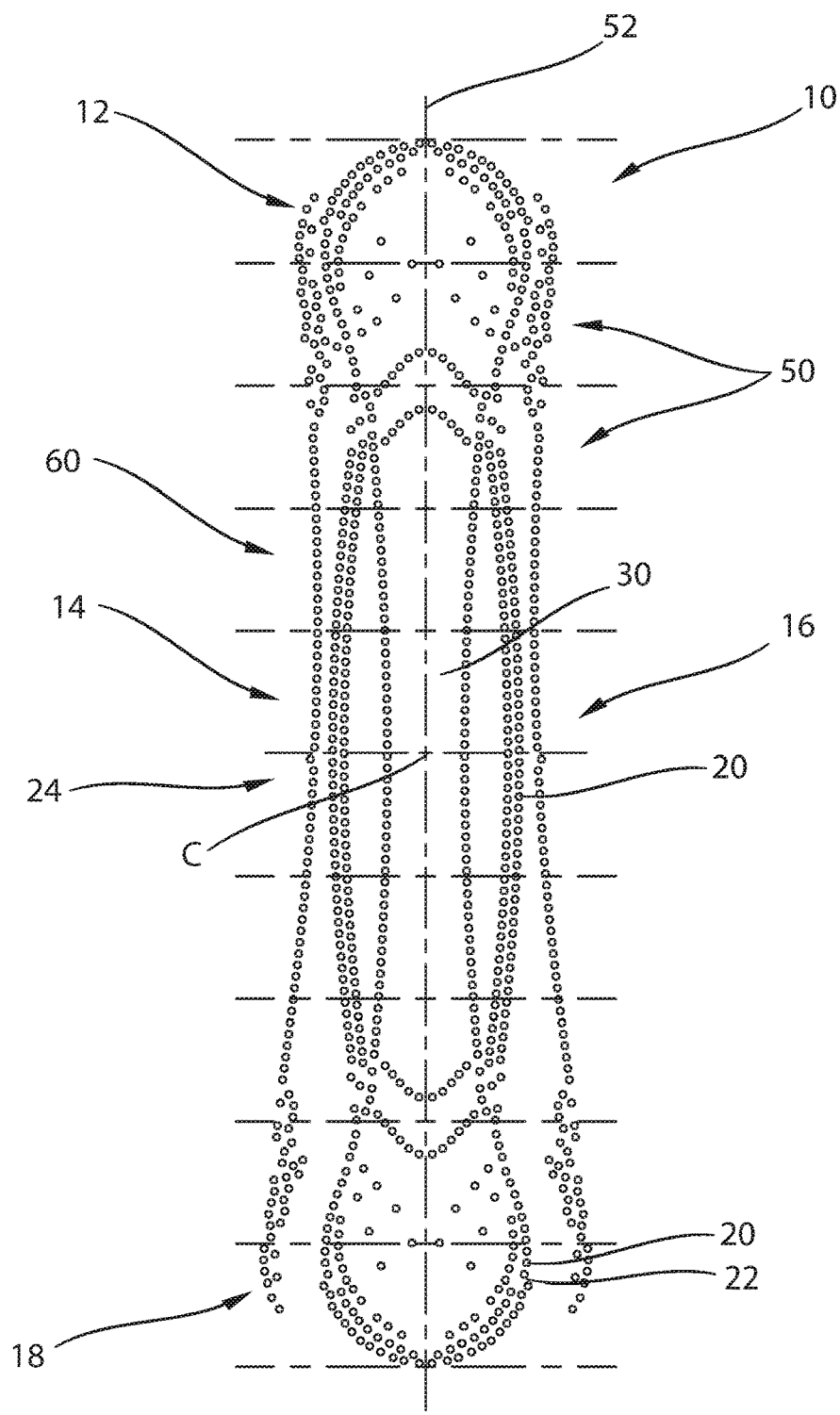
FIG. 6 is a schematic illustration of a bonding pattern in accordance with another embodiment of the disclosure.

As shown in FIG. 6, the bonding pattern 60 may be broken up into portions 50 of equal length along the longitudinal axis 52. In a non-limiting example, an article 10 with ten portions 50 of between about 25 and 40 mm portions can contains between about 70 to 100 bonding points, such as, for example, 75 bonding points, 80 bonding points, 81 bonding points, 82 bonding points, 83 bonding points, 84 bonding points, 85 bonding points, 86 bonding points, 87 bonding points, 88 bonding points, 89 bonding points, 90 bonding points, 91 bonding points, 92 bonding points, 93 bonding points, 94 bonding points, 95 bonding points, 96 bonding points, 97 bonding points, 98 bonding points, or 99 bonding points. In a non-limiting example, the bonding pattern 60 maintains a ratio of number of discrete bonding points to length in millimeters along the longitudinal axis of between about 1.7:1 to 4:1, such as, for example, 2.0:1, .2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, or 3.9:1. This ratio allows a reduction in tearing without undesirably increasing the stiffness of the web material.

Each portion 50 in the bonding pattern 60 may have between 0 and 30% more or less bonding points than the average for all the portions of the article. For example, a ten portion article wherein the average is 85 bonding points may not have less than 59 bonding points and no more than 110 bonding points in each portion 50.

In a non-limiting embodiment, the desired bonding pattern may be met by adding arcs at a set distance from the center of the article. The arcs may be spaced at a set distance from each other. For example, as shown in FIG. 6, a first arc may be placed in the central portion at about 160 mm to 190 mm from the center C of the absorbent article in one or both directions. Additional arcs can be located at 10 to 25 mm from the first arc. It has been found that arcs may prevent tearing as the article increases in size by maintaining the desired ratio of discrete bonding points to length along the longitudinal axis.

The bonding pattern may be designed to match the printing on the topsheet. In a non-limiting example, the bonding points are all in areas where the topsheet is printed. In a non-limiting example, the bonding points complement the printed pattern on the topsheet such that a percentage of the bonding points do not lie under printed areas of the topsheet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article comprising:
   A first end region and a second end region comprising a bonding pattern, wherein the first end region and the second end region are between 10% and 30% of the total area of the article,
   A central region that is between 40% to about 80% of the total surface area of the article, the bonding pattern adhering together a first web and a second web, the bonding pattern comprising a plurality of discrete bonding points and a sized spacing between each adjacent bonding point sufficient to have inscribed therein a circle having a diameter of about 3 mm to about 12 mm, wherein the bonding pattern is located solely in one of the front end region or the back end region, and
   wherein the article is a sanitary napkin.

2. The article of claim 1, wherein the sized spacing between each adjacent bonding point is sufficient to have inscribed therein a circle having a diameter of about 3 mm to about 10 mm.

3. The article of claim 1, wherein the bonding points comprise an adhesive.

4. The article of claim 1, wherein the bonding points have a shape selected from the group consisting of a circle, an ellipse, a rectangle, a triangle, and combinations thereof.

5. The article of claim 1, wherein the bonding points have a diameter in a range of about 1 mm to about 2 mm.

6. The article of claim 1, wherein the first web further comprises macroapertures.

7. The article of claim 1, wherein the second web is an absorbent structure.

8. The article of claim 1, wherein the bonding pattern covers about 5% to about 20% of the total surface area of the article.

9. The article of claim 1, wherein the bonding pattern adheres together both the first end regions of the first and second webs and the second end regions of the first and second webs, a first portion of the bonding pattern adheres together the first end regions of the first and second webs, a second portion of the bonding pattern adheres together the second end regions of the first and second webs.

10. The article of claim 1, wherein the bonding pattern comprises arcs that begin between 160 mm and 190 mm from the center point of the central region of the article and are spaced between are spaced between 10 to 25 mm apart.

11. The article of claim 10, wherein the arcs are located in the central region of the article.

12. The article of claim 10, wherein the spacing between adjacent arcs is about 10 to 25 mm.

13. The article of claim 10, wherein the bonding points of the arcs have a shape selected from the group consisting of a circle, an ellipse, a rectangle, a triangle, and combinations thereof.

14. The article of claim 10, wherein the bonding points of the arcs have a diameter of about 1 mm to about 2 mm.

15. An article comprising:
   A first end region and a second end region comprising a bonding pattern, wherein the first end region and the second end region are between 10% and 30% of the total area of the article,
   the bonding pattern adhering together a first web and a second web, the bonding pattern comprising a plurality of discrete bonding points and a sized spacing between each adjacent bonding point sufficient to have inscribed therein a circle having a diameter of about 3 mm to about 12 mm, wherein the bonding pattern is located solely in one of the front end region or the back end region, and
   wherein the article is a sanitary napkin.

16. The article of claim 15, wherein the sized spacing between each adjacent bonding point is sufficient to have inscribed therein a circle having a diameter of about 3 mm to about 10 mm.

17. The article of claim 15, wherein the bonding points comprise an adhesive.

18. The article of claim 15, wherein the bonding points have a shape selected from the group consisting of a circle, an ellipse, a rectangle, a triangle, and combinations thereof.

19. The article of claim 15, wherein the bonding points have a diameter in a range of about 1 mm to about 2 mm.

20. The article of claim 15, wherein the second web is an absorbent structure.

\* \* \* \* \*